(12) United States Patent
Kempf (10) Patent No.: US 9,029,119 B2
(45) Date of Patent: May 12, 2015

(54) COMPOSITION FOR THE CULTIVATION OF SOPHISTICATED BACTERIA

(75) Inventor: Volkhard Kempf, Dreieich-Buchschlag (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 1125 days.

(21) Appl. No.: 12/911,396

(22) Filed: Oct. 25, 2010

(65) Prior Publication Data

US 2011/0070627 A1   Mar. 24, 2011

Related U.S. Application Data

(63) Continuation of application No. PCT/EP2009/002790, filed on Apr. 16, 2009.

(30) Foreign Application Priority Data

Apr. 29, 2008   (DE) .......................... 10 2008 022 333

(51) Int. Cl.
*C12N 1/20*   (2006.01)

(52) U.S. Cl.
CPC ........................................ *C12N 1/20* (2013.01)

(58) Field of Classification Search
None
See application file for complete search history.

(56) References Cited

U.S. PATENT DOCUMENTS

2002/0162126 A1* 10/2002 Beach et al. ...................... 800/8

FOREIGN PATENT DOCUMENTS

WO   03/012058   2/2003

OTHER PUBLICATIONS

"Growth and Maintenance of Insect Cell lines" Invitrogen Life Technologies Publication, Version K, published Jul. 12, 2002, No. 25-0127. 38 pages.*
Centers of Disease Control and Prevention (CDC) (1999), Serodiagnosis of Emerging Infectious Diseases: *Bartonella* and *Ehrlichia* Infections (course manual).
International Preliminary Report on Patentability for Application No. PCT/EP2009/002790, Issued Nov. 9, 2010.
Zhang, P., et al. (2004), A family of variably expressed outer-membrane proteins (Vomp) mediates adhesion and autoaggregation in *Bartonella quintana*. Proc. Natl. Acad. Sci. USA 101:13630-13635.
Dauga, C., et al. (1996), Identification of *Bartonella henselae* and *B. quintana* 16s rDNA sequences by branch-, genus- and species-specific amplification. J. Med. Microbiol. 45: 192-199.
Dehio, C. (2005) *Bartonella*-host-cell interactions and vascular tumour formation. Nat. Rev. Microbiol. 3:621-631.
Drancourt, M. et al. (1996), New serotype of *Bartonella henselae* in endocarditis and cat-scratch disease. Lancet 347:441-443.
Eremeeva, M.E., et al., (2007), Bacteremia, fever and spenomegaly caused by a newly recognized *Bartonella* species, N. Engl. J. Med. 256:2381-2387.
Jones, et al., "Use of an insect cell culture growth medium to isolate bacteria from horses with effusive, fibrinous periarditis: A preliminary study." Veterinary Microbiology, Elsevier BV, NL, vol. 121, No. 1-2, Feb. 28, 2007, pp. 177-181, XP005914469 ISSN: 0378-1135.
Kempf, V.A. et al. (2001) Evidence of a leading role for VEGF in *Bartonella henselae*-induced endothelial cell proliferations. Cell. Microbiol. 3:623-632.
Kempf, V.A., et al. (2000) Interaction of *Bartonella henselae* with endothelial cells results in rapid bacterial rRNA synthesis and replication. Cell. Microbiol. 2:431-441.
La Scola, B. and D. Raoult (1999), Culture of *Bartonella quintana* and *Bartonella henselae* from human samples: a 5-year experience (1993 to 1998). J. Clin. Microbiol. 37:1899-1905.
Maggi, Ricardo G, et al., "Novel chemically modified liquid medium that will support the growth of seven *Bartonella* species." Journal of Clinical Microbiology Jun. 2005, vol. 43, No. 6, Jun. 2005, pp. 2651-2655, XP002536816 ISSN: 0095-1137.
Maurin, M. (1994), Isolation and characterization by immunofluorescence, sodium dodecyl sulfate-polyacrylamide gel electrophoresis, western blot, restriction fragment length polymorphism-PCR, 16S rRNA gene sequencing and pulsed-field gel electrophoresis of *Rochalimaea quintana* from a patient with bacillary angiomatosis. J. Clin. Microbiol. 32:1166-1171.
Product Information S0146 "Schneider's insect medium," SIGMA-Aldrich, St. Louis, Missouri, USA.
Product Information, "Schneider *Drosophila*, revised," SERVA Electrophoresis GmbH, Heidelberg, Deutschland, Cat.-No. 47521.
Riess, T. (2007), Analysis of *Bartonella* adhesion , A expression reveals differences between various *B. henselae* strains. Infect. Immun. 75:35-43.
Riess, T., et al. (2004), *Bartonella* adhesion A mediates a proangiogenic host cell response. J. Exp. Med. 200:1267-1278.
Riess, Tanja, et al., "Analysis of a novel insect cell culture medium-based growth medium for *Bartonella* species." Applied and Environmental Microbiology, Aug. 2008, vol. 74, No. 16, Aug. 2008, pp. 5224-5227.
Schneider, I. (1972), Cell lines derived from late embryonic stages of *Drosophila melanogaster*. J. Embryol. Exp. Morphol. 27:353-365.
Schneider, I. and A. Blumenthal (1978), *Drosophila* cell and tissue culture. In: Biology and genetics of *Drosophila*, vol. 2A, M. Ashburner and T.R.F. Wright Hsg., Academic Press, New York, pp. 266-315.
Schwartzman, W.A. et al., "Development and evaluation of a blood-free medium for determining growth curves and optimizing growth of *Rochalimaea henselae*." Journal of Clinical Microbiology, Jul. 1993, vol. 31, No. 7, Jul. 1993, pp. 1882-1885.
Weiss, E., et al. (1978), Vole agent identified as a strain of the trench *Rickettsia, Rochalimaea quintana*. Infect. Immun. 19:1013-1020.

* cited by examiner

*Primary Examiner* — Allison Fox
(74) *Attorney, Agent, or Firm* — Casimir Jones S.C.

(57) ABSTRACT

The present invention relates to a composition for the cultivation of sophisticated bacteria, preferably of the genus *Bartonella*, and to a method for the cultivation of these bacteria.

9 Claims, 8 Drawing Sheets

COMPOSITION FOR THE CULTIVATION OF SOPHISTICATED BACTERIA

CROSS-REFERENCES AND RELATED APPLICATIONS

This application is a continuation of copending International Patent Application PCT/EP 2009/002790 filed on Apr. 16, 2009 and designating the United States, which was not published under PCT Article 21(2) in English, and claims priority of German Patent Application DE 10 2008 022 333.6 filed on Apr. 29, 2008, which is incorporated herein by reference.

BACKGROUND OF THE INVENTION

1. Field of the Invention

The present invention relates to a composition for the cultivation of sophisticated bacteria, preferably of the genus Bartonella, and to a method for the cultivation of said bacteria.

2. Related Prior Art

The cultivation of sophisticated bacteria is a known problem of the microbiology and the medical diagnostics. The bacterium belonging to the genus Bartonella is such a sophisticated bacterium. Bartonella are important pathogens of the human and veterinary medicine. At the present time Bartonella henselae and Bartonella quintana are assumed being the most relevant Bartonella species being pathogenic for humans, which cause diseases such as the cat scratch disease, bacillary angiomatosis, trench fever and many others; cf. Dehio, C. (2005), Bartonella-host-cell interactions and vascular tumour formation. Nat. Rev. Microbiol. 3:621-631. Recently, new pathogens were described having an unclear epidemiology, e.g. Bartonella rochalimeae; cf. Eremeeva, M. E. et al. (2007), Bacteremia, fever and spenomegaly caused by a newly recognized Bartonella species. N. Engl. J. Med. 256:2381-2387. Bartonella spp., e.g. Bartonella henselae, Bartonella vinsonii subsp. berkhoffii, Bartonella schoenbuchiensis and many others can be found in a broad spectrum of mammalians, including cats, dogs, ruminant animals and rodents, which either suffer from these infections or act as asymptotic reservoir hosts for zoonoses.

It is known that bacteria of the genus Bartonella can only be cultivated very poorly. The diagnostics of Bartonella infections is therefore usually realized by the use of serological methods or by molecular methods, e.g. via the amplification of the 16S rDNA; cf. Centers of Disease Control and Prevention (CDC) (1999), Serodiagnosis of Emerging Infectious Diseases: Bartonella and Ehrlichia Infections (course manual), and Dauga, C. et al. (1996), Identification of Bartonella henselae and B. quintana 16s rDNA sequences by branch-, genus- and species-specific amplification. J. Med. Microbiol. 45:192-199.

Bartonella spp. are usually cultivated by using highly supplemented blood agar, e.g. chocolate agar, sheep blood agar or boiled blood agar. The use of these agars has the disadvantage that the incubation times are very long, namely up to 45 days, resulting in contamination problems; cf. Maurin, M. (1994), Isolation and characterization by immunofluorescence, sodium dodecyl sulfate-polyacrylamide gel electrophoresis, western blot, restriction fragment length polymorphism-PCR, 16S rRNA gene sequencing, and pulsed-field gel electrophoresis of Rochalimaea quintana from a patient with bacillary angiomatosis. J. Clin. Microbiol. 32:1166-1171. Until to this day the slow growth on solid agar based media limits experiments for the molecular analysis of the pathogenity of Bartonella henselae.

In the WO 03/012058 a medium for the cultivation of sophisticated microorganisms, such as Bartonella spp., is described. This medium, however, has also the disadvantage that the microorganisms only show a very slow growth. In addition, the medium consists of 20 individual substances making the production very complicated and susceptible to faults. The medium requires the addition of sheep blood making the suspension cloudy and, therefore, does not allow the evaluation of the optical density. The use of this medium within the context of an automated measuring of the growth of the sophisticated bacteria is, therefore, hardly possible, since this measuring is generally based on the acquisition of the optical densities of the cultures. Therefore, a corresponding limitation exists for examinations on the sensitivity of the sophisticated bacteria against antibiotics since here in the most cases optical measurings are performed as well.

SUMMARY OF THE INVENTION

Against this background it is an objective of the present invention to provide a new composition for the cultivation of sophisticated bacteria by means of which the disadvantages of the prior art are avoided. In particular, a liquid culture medium should be provided which enables a rapid growth of sophisticated bacteria and which, at the same time, can be produced in a cost-effective way.

This objective is achieved by the provision of a composition which comprises insect cell culture medium and fetal calf serum (FCS).

The inventors have surprisingly realized that sophisticated bacteria can be cultivated in a particularly rapid and well manner in media which, so far, have been used for the cultivation of insect cells, and which were supplemented by FCS.

This finding was surprising. In the prior art it is described that Bartonella henselae grows faster if it is co-incubated with host cells; cf. Kempf, V. A. et al. (2000), Interaction of Bartonella henselae with endothelial cells results in rapid bacterial rRNA synthesis and replication. Cell. Microbiol. 2:431-441; La Scola, B. and D. Raoult (1999), Culture of Bartonella quintana and Bartonella henselae from human samples: a 5-year experience (1993 to 1998). J. Clin. Microbiol. 37:1899-1905; and Weiss, E. et al. (1978), Vole agent identified as a strain of the trench rickettsia, Rochalimaea Quintana. Infect. Immun. 19:1013-1020. However, the authors have not realized that the sophisticated bacteria also grow in insect cell culture media in the absence of host cells upon the addition of FCS.

According to the invention a "composition for the cultivation" refers to a culture or cultivation medium for biological material. The cultivation medium can be used to maintain sophisticated bacteria in a vital state, to let them grow and/or to isolate them. The cultivation medium can be a liquid, semi-liquid or solid cultivation medium, whereas a liquid medium is preferred.

According to the invention "sophisticated bacteria" refer to such bacteria which are persistent against a cultivation in conventional media, such as LB broth, Dulbecco's modified Eagle's medium, F12 medium or the like. For this reason they are so far cultivated in highly supplemented blood agars, such as chocolate agar, sheep blood agar or boiled blood agar. Also in these media the sophisticated bacteria only show a very slow growth. Sophisticated bacteria require more stringent conditions with respect to the chemical composition of the cultivation media than non-sophisticated or modest bacteria. For example, sophisticated bacteria require the provision of specific organic molecules in the medium since they comprise a damaged or insufficient enzymatic machinery for the synthesis of nutrients such as vitamins, amino acids, lipids, cofactors such as NAD and NADH, nucleosides or capture molecules for free radicals etc. Alternatively or in addition the sophisticated bacterium can require specific organic molecules to be provided in the medium, or because of an intolerance of the bacterium for particular components, e.g. sugar, the lack of such molecules.

The sophisticated bacterium can be a bacterium damaged by reason of stress after the induction in the host or can be an impaired bacterium, e.g. as a result of an antibacterial mechanism of the host, because of antibiotics or the production of surfactant by the lung; such bacteria are also referred to as immunologically impaired bacteria. For example, the bacterium can comprise an impairment of the cell wall or of the cell wall synthesis. In addition transportation mechanisms or cellular metabolic pathways can be disordered as a result of a damage of or stress for the bacterium. Alternatively, the sophisticated bacterium can be a viable, however, according to the methods known in the prior art, not cultivable bacterium that represents a metabolically inactive form of a cultivable bacterium. Damaged bacteria which are exposed to stress or metabolically inactive bacteria are more resistant or imperishable for standard cultivation or isolation technologies. Alternatively, the sophisticated bacteria can be such bacteria which have been adapted to the environment of the host and do no longer tolerate cultivation conditions which deviate significantly from the conditions within the host.

Examples for sophisticated bacteria are such of the genus *Bartonella*, *Bordetella* spp., *Borrelia* spp. *Anaplasma* spp. and *Mycobacterium* spp.

According to the invention, "insect cell culture medium" refers to such a cultivation medium which is provided in the prior art for the cultivation of insect cells. Examples for such media are Schneider's medium, Schneider's modified serum ("Schneider's *Drosophila* revised"), Grace's medium, IPL-41-medium, TMN-FH medium, and TC-100 medium.

"Fetal calf serum" (FCS), also referred to as "feral bovine serum" (FBS) or newborn calf serum (NCS), is a liquid composition which is obtained from cow fetuses. It contains a vast number of proteins, not all of which are known today. The main component is "bovine serum albumin" or "BSA", a globular protein consisting of 584 amino acids and comprising a relative molecular mass of approximately 64.500. Further proteins are e.g. growth factors. They represent the main component of fetal calf serum (FCS).

The objective underlying the invention is completely solved by the provision of a composition which comprises insect cell culture medium and FCS. The medium provided by the inventors is simple in its production and allows a relatively rapid planktonic growth of the sophisticated bacteria.

For this reason the medium according to the invention is a prerequisite for the development of rapid diagnostic methods for the detection of pathogenic sophisticated bacteria. The molecular analysis of the pathogenicity of sophisticated bacteria is now also possible in an improved manner. Another advantage of the composition according to the invention is the fact that it does not contain haemin since it is known that specific sophisticated bacteria, such as of the genus *Bartonella*, only tolerate particular concentrations of haemin; cf. Schwartzman, W. A. et al. (1993), Development and evaluation of a blood-free medium for determining growth curves and optimizing growth of *Rochalinaea henselae*. J. Clin. Microbiol. 31:1882-1885.

In this context it is preferred if the sophisticated bacteria are such of the genus *Bartonella*.

This measure has the advantage that a composition comprising such a particularly sophisticated bacteria species is provided, which is involved in a plurality of human and veterinary diseases.

It is further preferred if the insect cell culture medium is modified Schneider's *Drosophila* medium.

This measure has the advantage that such an insect cell culture medium is used which, according to the findings of the inventors, is particularly suited. The composition of modified Schneider's *Drosophila* medium is for example disclosed in Schneider, I. and A. Blumenthal (1978), *Drosophila* cell and tissue culture. In: Biology and genetics of *Drosophila*, Vol. 2A, M. Ashburner and T. R. F. Wright Hsg., Academic Press, New York, pages 266-315, in particular page 308; and in Schneider, I. (1972), Cell lines derived from late embryonic stages of *Drosophila melanogaster*. J. Embryol. Exp. Morphol. 27: 353-365; and in the product information S 0146 "Schneider's insect medium" SIGMA-Aldrich, St. Louis, Mo., USA; and the product information "Schneider *Drosophila*, revised", SERVA Electrophoresis GmbH, Heidelberg, Deutschland; Kat.-Nr. 47521. The content of the before-identified publications is incorporated by reference and part of the present disclosure.

In this context it is preferred if the composition according to the invention comprises the following components:

| Inorganic salts, namely | |
| --- | --- |
| CaCl$_2$ (anhydrous) [in mg/l H$_2$O]: | approx. 50 to approx. 2000, |
| KCl [in mg/l H$_2$O]: | approx. 200 to approx. 3000, |
| KH$_2$PO$_4$ [in mg/l H$_2$O]: | approx. 30 to approx. 1500, |
| MgSO$_4$•7H$_2$O [in mg/l H$_2$O]: | approx. 1000 to approx. 6000, |
| NaCl [in mg/l H$_2$O]: | approx. 300 to approx. 4000, |
| NaHCO$_3$ [in mg/l H$_2$O]: | approx. 25 to approx. 1300, |
| Na$_2$HPO$_4$ [in mg/l H$_2$O]: | approx. 60 to approx. 2500, |
| amino acids, namely | |
| β-alanine [in mg/l H$_2$O]: | approx. 30 to approx. 1800, |
| L-arginine [in mg/l H$_2$O]: | approx. 50 to approx. 2000, |
| L-aspartic acid [in mg/l H$_2$O]: | approx. 25 to approx. 1300, |
| L-cysteine [in mg/l H$_2$O]: | approx. 5 to approx. 200, |
| L-cysteine•2HCl [in mg/l H$_2$O]: | approx. 2 to approx. 150, |
| L-glutamine [in mg/l H$_2$O]: | approx. 250 to approx. 3500, |
| L-glutamic acid [in mg/l H$_2$O]: | approx. 75 to approx. 2600, |
| glycine [in mg/l H$_2$O]: | approx. 20 to approx. 1000, |
| L-histidine [in mg/l H$_2$O]: | approx. 25 to approx. 1300, |
| L-isoleucine [in mg/l H$_2$O]: | approx. 10 to approx. 400, |
| L-leucine [in mg/l H$_2$O]: | approx. 10 to approx. 400, |
| L-lysine•HCl [in mg/l H$_2$O]: | approx. 200 to approx. 3000, |
| L-methionine [in mg/l H$_2$O]: | approx. 10 to approx. 400, |
| L-proline [in mg/l H$_2$O]: | approx. 250 to approx. 3500, |
| L-serine [in mg/l H$_2$O]: | approx. 20 to approx. 1000, |
| L-threonine [in mg/l H$_2$O]: | approx. 25 to approx. 1300, |
| L-tryptophan [in mg/l H$_2$O]: | approx. 10 to approx. 400, |
| L-tyrosine [in mg/l H$_2$O]: | approx. 30 to approx. 1800, |
| L-valine [in mg/l H$_2$O]: | approx. 20 to approx. 1000, |
| other components, namely | |
| malic acid [in mg/l H$_2$O]: | approx. 5 to approx. 200, |
| succinic acid [in mg/l H$_2$O]: | approx. 50 to approx. 2000, |
| fumaric acid [in mg/l H$_2$O]: | approx. 5 to approx. 200, |
| glucose [in mg/l H$_2$O]: | approx. 300 to approx. 4000, |
| yeast extract [in mg/l H$_2$O]: | approx. 300 to approx. 4000, |
| α-ketoglutaric acid [in mg/l H$_2$O]: | approx. 25 to approx. 1300, |
| α-trehalose [in mg/l H$_2$O]: | approx. 300 to approx. 4000, and |
| fetal calf serum (FCS) [in vol.-%] | approx. 1 to approx. 25. |

This measure has the advantage that the most important parameters of the composition according to the invention are provided and enable a simple production for the skilled person.

According to a preferred embodiment the composition according to the invention comprises the following components:

| Inorganic salts, namely | |
| --- | --- |
| CaCl$_2$ (anhydrous) [in mg/l H$_2$O]: | approx. 600, |
| KCl [in mg/l H$_2$O]: | approx. 1600, |
| KH$_2$PO$_4$ [in mg/l H$_2$O]: | approx. 450, |
| MgSO$_4$•7H$_2$O [in mg/l H$_2$O]: | approx. 3700, |
| NaCl [in mg/l H$_2$O]: | approx. 2100, |
| NaHCO$_3$ [in mg/l H$_2$O]: | approx. 400, |
| Na$_2$HPO$_4$ [in mg/l H$_2$O]: | approx. 700, |
| amino acids, namely | |
| β-alanine [in mg/l H$_2$O]: | approx. 500, |
| L-arginine [in mg/l H$_2$O]: | approx. 600, |
| L-aspartic acid [in mg/l H$_2$O]: | approx. 400, |
| L-cysteine [in mg/l H$_2$O]: | approx. 60, |
| L-cysteine•2HCl [in mg/l H$_2$O]: | approx. 21.7, |
| L-glutamine [in mg/l H$_2$O]: | approx. 1800, |
| L-glutamic acid [in mg/l H$_2$O]: | approx. 800, |
| glycine [in mg/l H$_2$O]: | approx. 250, |
| L-histidine [in mg/l H$_2$O]: | approx. 400, |
| L-isoleucine [in mg/l H$_2$O]: | approx. 150, |
| L-leucine [in mg/l H$_2$O]: | approx. 150, |
| L-lysine•HCl [in mg/l H$_2$O]: | approx. 1650, |
| L-methionine [in mg/l H$_2$O]: | approx. 150, |
| L-proline [in mg/l H$_2$O]: | approx. 1750, |
| L-serine [in mg/l H$_2$O]: | approx. 250, |
| L-threonine [in mg/l H$_2$O]: | approx. 350, |
| L-tryptophan [in mg/l H$_2$O]: | approx. 100, |
| L-tyrosine [in mg/l H$_2$O]: | approx. 500, |
| L-valine [in mg/l H$_2$O]: | approx. 300, |
| other components, namely | |
| malic acid [in mg/l H$_2$O]: | approx. 60, |
| succinic acid [in mg/l H$_2$O]: | approx. 600, |
| fumaric acid [in mg/l H$_2$O]: | approx. 60, |
| glucose [in mg/l H$_2$O]: | approx. 2000, |
| yeast extract [in mg/l H$_2$O]: | approx. 2000, |
| α-ketoglutaric acid [in mg/l H$_2$O]: | approx. 350, |
| α-trehalose [in mg/l H$_2$O]: | approx. 2000, and |
| fetal calf serum (FCS) [in vol.-%] | approx. 10. |

This measure has the advantage that the exact concentrations of the composition according to the invention are provided, which, according to the findings of the inventors, yield in particularly good results.

It is furthermore preferred if the composition additionally comprises approximately 0.5 to approximately 50% (w/v), further preferred approximately 5% (w/v) sucrose.

The inventors have realized that sophisticated bacteria of the genus *Bartonella* grow even better in the composition according to the invention if it is supplemented with sucrose in the indicated concentration ranges. Surprisingly, for example the addition of other carbohydrates, such as mannose or galactose, actually result in a deterioration of the growth of the bacteria.

It is further preferred if the composition according to the invention comprises an pH value that is at approximately 5.5 to approximately 7.7, further preferred at approximately 6.5.

This measure has the advantage that at the indicated pH value a particularly well solubility of the components is realized and for example precipitations can be largely avoided. This applies in particular for a pH value of 6.5.

It is further preferred if the composition according to the invention is sterilized.

This measure has the advantage that when using the composition according to the invention contaminations, e.g. by non-sophisticated bacteria, can be avoided.

A further subject matter of the present invention relates to a method for the cultivation of sophisticated bacteria, which comprises the following steps: (1) providing a composition for the cultivation of sophisticated bacteria, (2) inoculating the composition with sophisticated bacteria, preferably such of the genus *Bartonella*, preferably with approximately $1 \times 10^5$ to approximately $1 \times 10^6$ bacteria cells, (3) incubating the composition with bacteria under cultivation conditions, preferably for approximately 1 to 20 days, and preferably at approximately 37° C. and preferably in an atmosphere comprising 5 vol.-% CO$_2$, whereas as composition the before-described composition according to the invention is used.

By doing so, the inventors provide a particularly well-suited method for the cultivation of sophisticated bacteria, by means of which within a very short period a bacteria culture can be obtained.

It goes without saying that the features named above and those still to be explained below can be used not only in the respectively specified combination, but also in other combinations or on their own without departing from the scope of the present invention.

The invention is now explained in more detail by means of embodiments resulting in further characteristics and advantages. The embodiments do not limit the scope of the invention. Reference is made to the enclosed figures.

DESCRIPTION OF PREFERRED EMBODIMENTS

1. Material and Methods
1.1 Bacterial Strains and Growth Conditions

*Bartonella henselae* Marseille Drancourt, M. et al. (1996), New serotype of *Bartonella henselae* in endocarditis and cat-scratch disease. Lancet 347:441-443), *Bartonella henselae* BadA⁻ (not expressing adhesin A; (Riess, T. et al. (2004), *Bartonella* adhesion A mediates a proangiogenic host cell response. J. Exp. Med. 200:1267-1278), *Bartonella henselae* Houston-1 (ATCC 49882), *Bartonella quintana* Toulouse (collection of the Institute Pasteur, Paris, France), *Bartonella quintana* JK31 (Zhang, P. et al. (2004), A family of variably expressed outer-membrane proteins (Vomp) mediates adhesion and autoaggregation in *Bartonella quintana*. Proc. Natl. Acad. Sci. U.S.A. 101:13630-13635) and *Bartonella vinsonii* subsp. *Berkhoffii* (ATCC 51672) were routinely grown on Columbia blood agar (CBA) in a humidified atmosphere at 37° C. and 5% $CO_2$. *Bartonella henselae* BadA⁻ was grown in the presence of 25 µg/ml kanamycin. Unless stated otherwise, *Bartonella henselae* Marseille was used in all experiments. For the production of bacterial stock suspensions, bacteria were harvested from agar plates after 5 days of cultivation and frozen in Luria Bertani medium (LB) containing glycerol.

1.2 Growth of *Bartonella* spp. in Liquid Medium

The bacteria were grown in liquid media using cell culture flasks with constant slow shaking (60 rpm/min) in a humidified atmosphere at 37° C. and 5% $CO_2$. The following liquid media were tested for the growth of *Bartonella henselae*: brain heart medium (BH), LB broth, *Bartonella* alpha-proteobacteria growth medium (BAPGM), supplemented with 10 vol.-% fetal calf serum (FCS; Sigma-Aldrich, Munich, Germany) instead of 5 vol.-% defribrinated sheep blood, endothelial cell growth medium containing supplement mix (Promocell, Heidelberg, Germany) and Schneider's medium. In some experiments, the liquid media were supplemented with 10 vol.-% FCS. The liquid media were inoculated with $1\times10^5$ or with $1\times10^6$ bacteria/ml and the respective optical densities ($OD_{600\,nm}$) were assessed at 24 h intervals in triplicates. Additionally, the number of cultivated viable bacteria were determined by plating serial dilutions on CBA plates followed by an incubation period of 3 weeks.

Schneider's medium (Schneider's *Drosophila* powder medium, revised, Serva, Heidelberg, Germany, catalogue No. 47521) is composed as follows:

TABLE 1

Composition of the Schneider's medium

| Component | Concentration (mg/l) |
|---|---|
| Total weight without $NaHCO_3$ without $CaCl_2$ | 25.750 |
| Inorganic Salts | |
| $CaCl_2$ anhydrous | 600 |
| KCl | 1.600 |
| $KH_2PO_4$ | 450 |
| $MgSO_4\,7H_2O$ | 3.700 |
| NaCl | 2.100 |
| $NaHCO_3$ | 400 |
| $Na_2HPO_4$ | 700 |
| Amino Acid | |
| (beta)-alanine | 500 |
| L-arginine | 600 |
| Aspartic acid | 400 |
| L-cystine | 60 |
| L-cystine 2HCl | 21.7 |
| L-glutamine | 1.800 |
| glutamic acid | 800 |
| glycine | 250 |
| L-histidine | 400 |
| L-isoleucine | 150 |
| L-leucine | 150 |
| L-lysine HCl | 1.650 |
| L-methionine | 150 |
| L-proline | 1.750 |
| L-serine | 250 |
| L-threonine | 350 |
| L-tryptophan | 100 |
| L-tyrosine | 500 |
| L-valine | 300 |
| Other Components | |
| malic acid | 60 |
| succinic acid | 600 |
| fumaric acid | 60 |
| glucose | 2.000 |
| yeast extract | 2.000 |
| (alpha)-ketoglutaric acid | 350 |
| (alpha)-trehalose | 2.000 |

The medium was prepared according to the manufacturer's instruction:

For 1 l of medium approximately 800 ml distilled water was placed in a volumetric flask. 24.45 g of the powder medium was added while stirring. For a better dissolving the solution can be heated to 35° C. 0.4 g sodium bicarbonate and 0.6 g calcium chloride are each dissolved in approximately 10 ml distilled water and were slowly added to the medium while stirring. A pH value of 6.5 was adjusted with 1 N NaOH or 1 N HCl while stirring. Fill up with distilled water to 1 l, supplement with 10% FCS and perform a sterile filtering.

To test for an optimal bacterial growth, 5% (w/v) of either sucrose (Riedel de Haën, Seelze, Germany), glucose (Sigma), fructose (Merck, Darmstadt, Germany), galactose (Merck) or mannose (Sigma) were added, respectively.

1.3 Electron Microscopy

Schneider's medium containing 10 vol.-% FCS was inoculated with *Bartonella henselae* Marseille ($1 \times 10^6$/ml). After 4 days of growth, the bacterial culture was fixed with 2.5% glutaraldehyde in phosphate-buffered saline (PBS) for 15 minutes at 37° C. and stored for 24 hours at 4° C. The fixed cells were embedded in 2% agarose and cubic blocks of about 1 mm in length were cut out. After post-fixation with 1% osmium tetraoxide in 100 mM $PO_4$ buffer, pH 7.2, for one hour on ice, these blocks were rinsed with bi-distilled water, treated with 1% aqueous uranylacetate for one hour at 4° C., dehydrated through a graded series of ethanol and embedded in Epon. The sections were stained with 1% aqueous uranylacetate and leadcitrate and analyzed in a Philips CM10 electron microscope at 60 kV using a 30 µm objective aperture.

1.4 Precipitation of *Bartonella henselae* Proteins from the Liquid Culture Supernatant 10 ml of Schneider's medium supplemented with 10 vol.-% FCS were inoculated with *Bartonella henselae* ($1 \times 10^7$/ml) and incubated for 10 days. The bacterial cultures were centrifuged for 15 minutes at 3,000 g and proteins were precipitated from the supernatant by adding 10% trichloro acetic acid for one hour on ice followed by a centrifugation for 20 minutes at 20,000 g and 4° C. The resulting pellet was re-suspended three times in 1 ml ice cold acetone, incubated for 20 minutes on ice and centrifuged for 15 minutes at 20,000 g and 4° C. Finally, the resulting pellet was re-suspended in 700 µl distilled water and stored at −20° C. until further use.

1.5 Immunoblotting

BadA was detected in the precipitated protein fraction prepared of *Bartonella henselae* liquid culture supernatants by immunoblotting. After the addition of sodium dodecyl sulfate (SDS) sample buffer, the proteins were separated by 12% SDS-polyacrylamid gel electrophoresis and transferred onto nitrocellulose membranes (Schleicher and Schuell, Dassel, Germany). The membranes were blocked for one hour in 5% skim milk powder dissolved in 10 mM Tris pH 7.4, 0.15 M NaCl and 0.2% Tween 20, followed by an incubation with a specific BadA antibody (Riess, T. et al. (2004), *Bartonella* adhesion A mediates a proangiogenic host cell response. J. Exp. Med. 200:1267-1278) over night. Horseradish peroxidase conjugated secondary antibodies were used for the detection of anti-BadA IgG, and the signals were visualized with 3,3'-diaminobenzidine tetrahydro chloride (DAB; Applichem, Darmstadt, Germany).

1.6 Cultivation and Infection of the Host Cells

Human umbilical vein endothelial cells (HUVECs) were cultured in endothelial cell growth medium (PromoCell, Heidelberg, Germany) as described; cf. Riess, T. (2007), Analysis of *Bartonella* adhesin A expression reveals differences between various *B. henselae* strains. Infect. Immun. 75:35-43. For adherence and invasion experiments, $1 \times 10^5$ cells per well were seated onto collagen G-coated cover slips the day before the experiment. The cells were infected with *Bartonella henselae* either grown in liquid medium (Schneider's with 10 vol.-% FCS and 5% (w/v) sucrose) or with bacterial stocks grown on CBA at a multiplicity of infection (MOI) of 100. After 30 minutes (adhesion), 2 h and 24 h (invasion) cover slips were washed three times with pre-warmed endothelial cell medium and fixed in 3.75% paraformaldehyde (PFA).

The HeLa cells were grown in RPMI 1640 supplemented with 10% FCS and 2 mM glutamine. For the infection experiments, $1 \times 10^5$ cells per well were seated in 24-well cell culture dishes the day before the experiment. 2 hours before the infection, the medium was replaced by medium without antibiotics and FCS to avoid non-specific vascular endothelial growth factor (VEGF) production. The cells were infected with *Bartonella henselae* either grown in liquid medium (Schneider's with 10 vol.-% FCS and 5% (w/v) sucrose) or with bacterial stocks grown on CBA (MOI: 250, 500, and 1000). The bacteria were sedimented onto the cultured cells by centrifugation of 5 minutes at 300 g. 25 ng/ml phorbol-12-myristate-13-acetate (PMA, Sigma-Aldrich) was used as a positive control, to induce the secretion of VEGF-A. The supernatants for VEGF-A ELISAs were taken after 24 hours and centrifuged shortly to spin down insoluble particles.

1.7 Quantification of VEGF-A Secretion

The VEGF-A concentrations in the cell culture supernatants were quantified using a human VEGF-$A_{165}$ ELISA kit (R&D Systems, Wiesbaden, Germany) according to the manufacturer's instructions.

1.8 Immunostaining and Confocal Laser Scanning Microscopy (CLSM)

*Bartonella henselae* was re-suspended in PBS, dried on glass slides and fixed with 3.75% PBS-buffered PFA. The bacteria were stained as described previously using BadA specific primary antibodies and cyanine-dye (Cy)2-conjugated secondary antibodies (Dianova, Hamburg, Germany); cf. Riess, T. et al. (2004), *Bartonella* adhesin A mediates a proangiogenic host cell response, J. Exp. Med. 200: 1267-1278). The bacterial DNA was stained with 4',6-diamidin-2'-phenylindole-dihydrochloride (DAPI; Merck). The slides were analyzed with a Leica DMRE fluorescence microscope equipped with a Spot RT monochrome digital camera and the related Spot Advanced Software (Visitron, Puchheim, Germany).

For the microscopic analysis of host cell adhesion and invasion, differential staining of extra- and intra-cellular *Bartonella henselae* was performed as described before with few modifications; cf. Kempf, V. A. et al. (2000), Interaction of *Bartonella henselae* with endothelial cells results in rapid bacterial rRNA synthesis and replication. Cell. Microbiol. 2:431-441. Briefly, PFA-fixed cells were washed in PBS at the beginning and after each incubation step. Non-specific binding of antibodies was blocked with 0.2% bovine serum albumin in PBS for 15 minutes. The cells were first incubated with BadA-specific primary antibodies (Riess, T. et al. (2004) *Bartonella* adhesion A mediates a proangiogenic host cell response. J. Exp. Med. 200:1267-1278) followed by Cy2-conjugated secondary antibodies (Dianova). Next, the cells were permeabilized by incubation with 0.2% Triton X-100 in PBS for 15 minutes and incubated with the BadA-specific antibodies followed by Cy5-conjugated secondary antibodies (Dianova). Actin was stained with tetramethyl-rohdamin-isothiocyanate (TRITC)-labeled phalloidin (Sigma-Aldrich). Slides were embedded using mounting medium and analyzed with a Leica DM IRE 2 confokal laser scanning microscope. The images were digitally processed with Adope Photoshop 7.0 (Adobe Systems, Mountain View, Calif.).

1.9 Statistical Analysis

All experiments were performed in triplicate. The experiments were repeated and revealed comparable results.

2. Results
2.1 Development of a Liquid Growth Medium for *Bartonella henselae*

While analyzing the interaction of *Bartonella henselae* with insect cells (Schneider cells from *Drosophila melanogaster*; cf. Schneider, I. (1972), Cell lines derived from late embryonic stages of *Drosophila melanogaster*. J. Embryol. Exp. Morphol. 27:353-365) the inventors noticed growth of *Bartonella henselae* in the cell culture medium used in these experiments (Schneider's *Drosophila* powder medium (Serva) supplemented with 10 vol.-% FCS and 2 mM glutamine). As no easy-to-prepare liquid growth medium for *Bartonella* spp. was described before, the Schneider's medium was further evaluated for the use as a growth medium for *Bartonella*.

Figure 1:
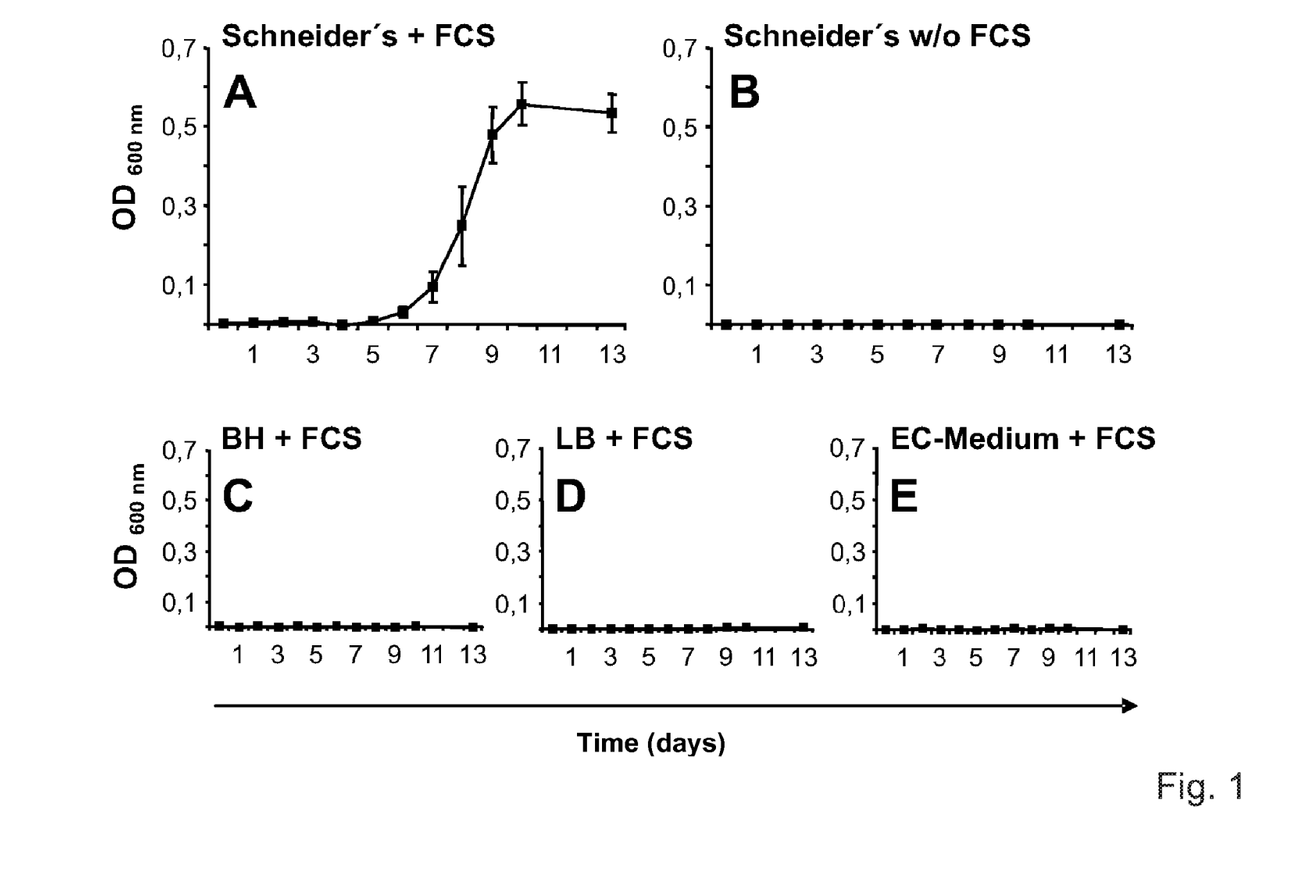
FIG. 1: Growth curves of *Bartonella henselae* in different liquid growth media. Several liquid growth media were inoculated with *Bartonella henselae* ($1 \times 10^5$/ml) and the bacterial growth was determined by measuring the optical density (OD$_{600\ nm}$) at 24 h intervals. (A) Schneider's medium with 10 vol.-% FCS, (B) pure Schneider's medium, (C) BH medium with 10 vol.-% FCS, (D) LB broth with 10 vol.-% FCS, (E) endothelial cell growth medium (EC) with 10 vol.-% FCS. It is to be noted that the growth of *Bartonella henselae* was only observed in Schneider's medium supplemented with 10 vol.-% FCS.

First, the growth of *Bartonella henselae* in Schneider's medium supplemented with FCS was compared with pure Schneider's medium. Both media were inoculated with *Bartonella henselae* ($1\times10^5$/ml) and incubated for 13 days. The bacterial growth was determined by measuring the optical density ($OD_{600\ nm}$) revealing a typical growth curve with a Lag phase, a logarithmic growth phase and a stationary phase in the FCS-supplemented medium (FIG. 1A), whereas pure Schneider's medium did not support *Bartonella henselae* growth (FIG. 1B).

As the addition of FCS to Schneider's medium was important for the bacterial growth, also the *Bartonella* growth in two microbiological standard media (LB, BH) and in endothelial cell growth medium which were all supplemented with 10 vol.-% FCS was investigated. Remarkably, none of these media supported the growth of *Bartonella henselae* (FIG. 1C-E).

Figure 2:
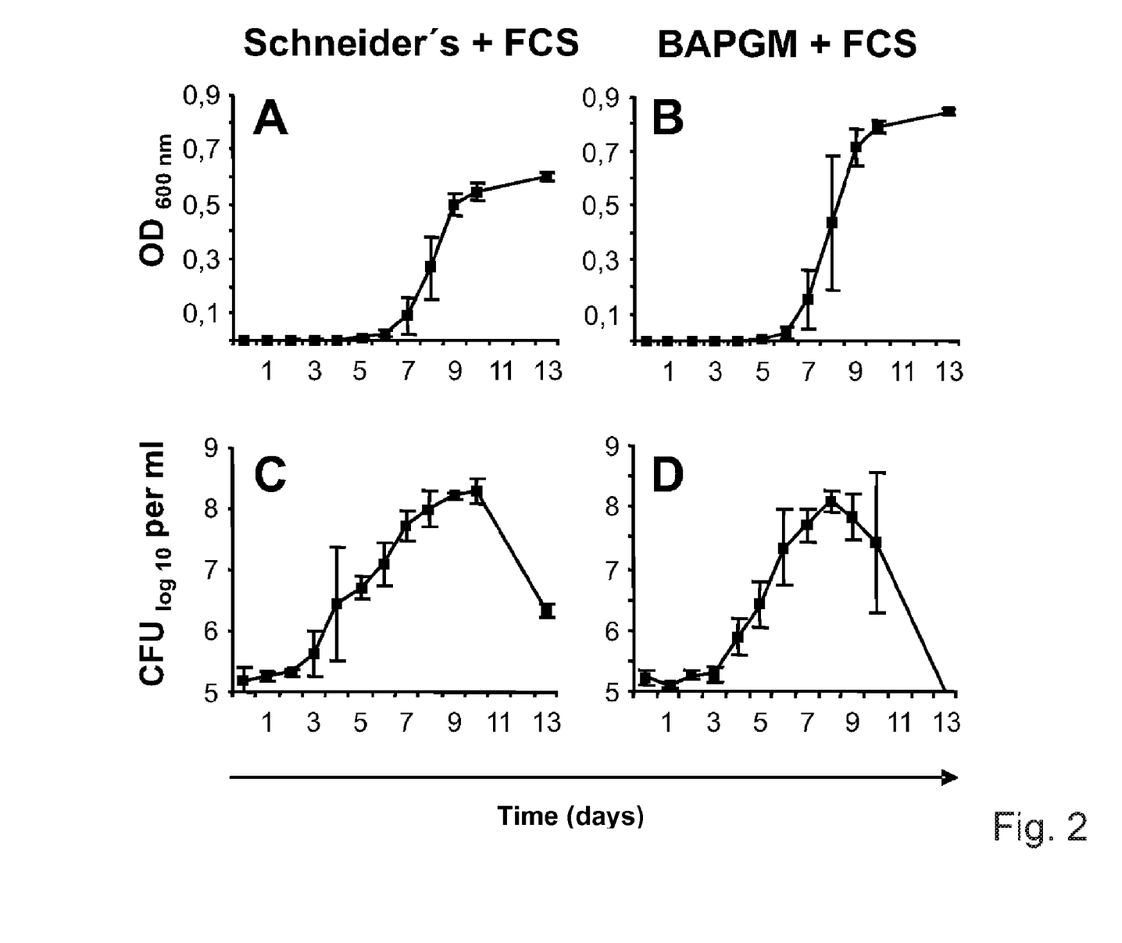
FIG. 2: Growth curves of *Bartonella henselae* in Schneider's medium and BAPGM. Both, Schneider's medium and BAPGM were supplemented with 10% FCS and inoculated with *Bartonella henselae* ($1 \times 10^5$/ml). The bacterial growth was determined by measuring the optical density (OD$_{600\ nm}$) at 24 h intervals (A, B). The number of viable bacteria (CFU/ml) was determined in parallel by plating serial dilutions on CBA (C, D).

Next, the growth of *Bartonella henselae* in Schneider's medium was compared with BAPGM (Maggi, R. G. et al. (2005), Novel chemically modified liquid medium that will support the growth of seven *Bartonella* species. J. Clin. Microbiol. 43:2651-2655), each supplemented with 10 vol.-% FCS. Both media were inoculated with *Bartonella henselae* ($1\times10^5$/ml) and incubated for 13 days. The growth of the bacteria was determined by measuring the optical density (FIG. 2A, B) and by counting the number of viable bacteria (CFU/ml) at the same time points (FIG. 2C, D). The OD values showed a similar course in both media although the final OD was higher in BAPGM with 10% FCS in comparison with Schneider's with 10 vol.-% FCS (0.84 vs. 0.60).

The determination of the bacterial numbers showed a lag phase of 2-3 days followed by an exponential growth phase in both media. The maximum bacterial numbers were slightly higher in Schneider's medium containing 10 vol.-% FCS compared to BAGPM with 10 vol.-% FCS ($1.9\times10^8$ vs. $1.2\times10^8$ CFU/ml). After the exponential growth phase, the number of viable bacteria decreased rapidly (death phase) with no detectable stationary phase; such a lack of a stationary phase was described already earlier for *Bartonella henselae*; cf. Maggi, R. G. (2005), Novel chemically modified liquid medium that will support the growth of seven *Bartonella* species. J. Clin. Microbiol. 43:2651-2655.

Figure 3:
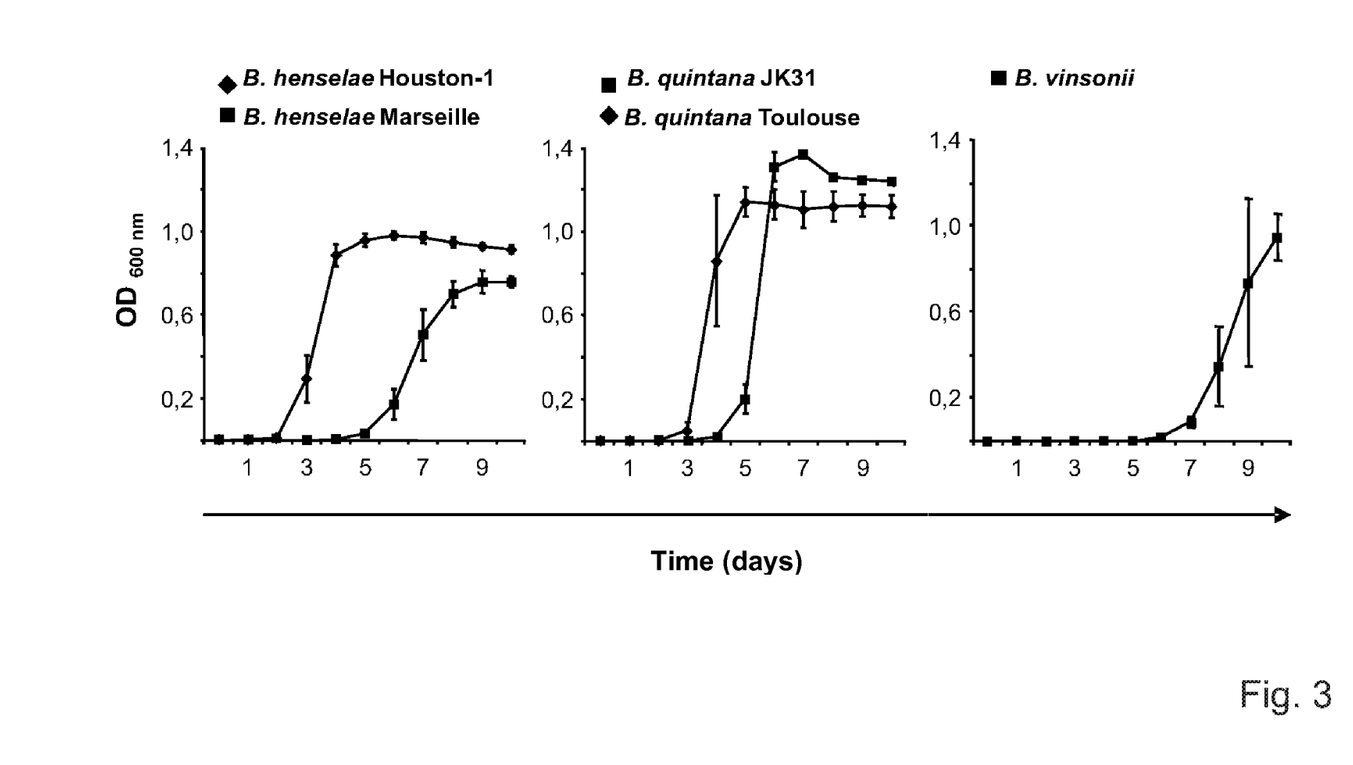
FIG. 3: Growth curves of different *Bartonella* strains in Schneider's medium. Schneider's medium with 10 vol.-% FCS was inoculated with *Bartonella henselae* Marseille, *Bartonella henselae* Houston-1, *Bartonella quintana* Toulouse, *Bartonella* JK31 and *Bartonella vinsonii* ($1 \times 10^5$ bacteria/ml) and bacterial growth was determined by measuring the optical density (OD$_{600\ nm}$) at 24 h intervals. It is to be noted that all strains exhibit growth in this medium although the intervals before the start of the logarithmic growth (lag phase) and the maximum optical density differ.

2.2 Growth of Different *Bartonella* spp. in Schneider's Medium Containing 10 Vol.-% FCS Next, the growth of other human medically and veterinary important *Bartonella* spp. was analyzed, namely of *Bartonella henselae* Marseille, *Bartonella henselae* Houston-1, *Bartonella quintana* Toulouse, *Bartonella quintana* JK31, and *Bartonella vinsonii*. Again, Schneider's medium supplemented with 10 vol.-% FCS was inoculated with $1\times10^5$ bacteria/ml of each strain and incubated for 10 days (FIG. 3). All five strains showed bacterial growth but the time until they reached the respective exponential phase and the maximum optical densities differed (lag phase of two days for *Bartonella henselae* Houston-1, three days for *Bartonella quintana* Toulouse, four days for *Bartonella quintana* JK31, five days for *Bartonella henselae* Marseille, and six days for *Bartonella vinsonii*).

The best growing strain was *Bartonella quintana* JK31 ($OD_{600\ nm}$: 1.37 at day 7), the slowest growing strains were *Bartonella henselae* Marseille ($OD_{600\ nm}$: 0.76 at day 9), and *Bartonella vinsonii* ($OD_{600\ nm}$: 0.95 at day 10). These data indicate that even within a certain species, the generation times and maximum growth rates can differ significantly (e.g. for *Bartonella henselae* Houston-1 and *Bartonella henselae* Marseille).

2.3 Improvement of Schneider's Based *Bartonella* Growth Medium

While evaluating different methods for genetic manipulation of *Bartonella henselae*, the inventors realized that the addition of sucrose to Schneider's medium with 10 vol.-% FCS resulted in an even faster bacterial growth. Therefore, it was more systematically tested the influence of several carbohydrates on the growth rates of *Bartonella henselae*.

Figure 4:
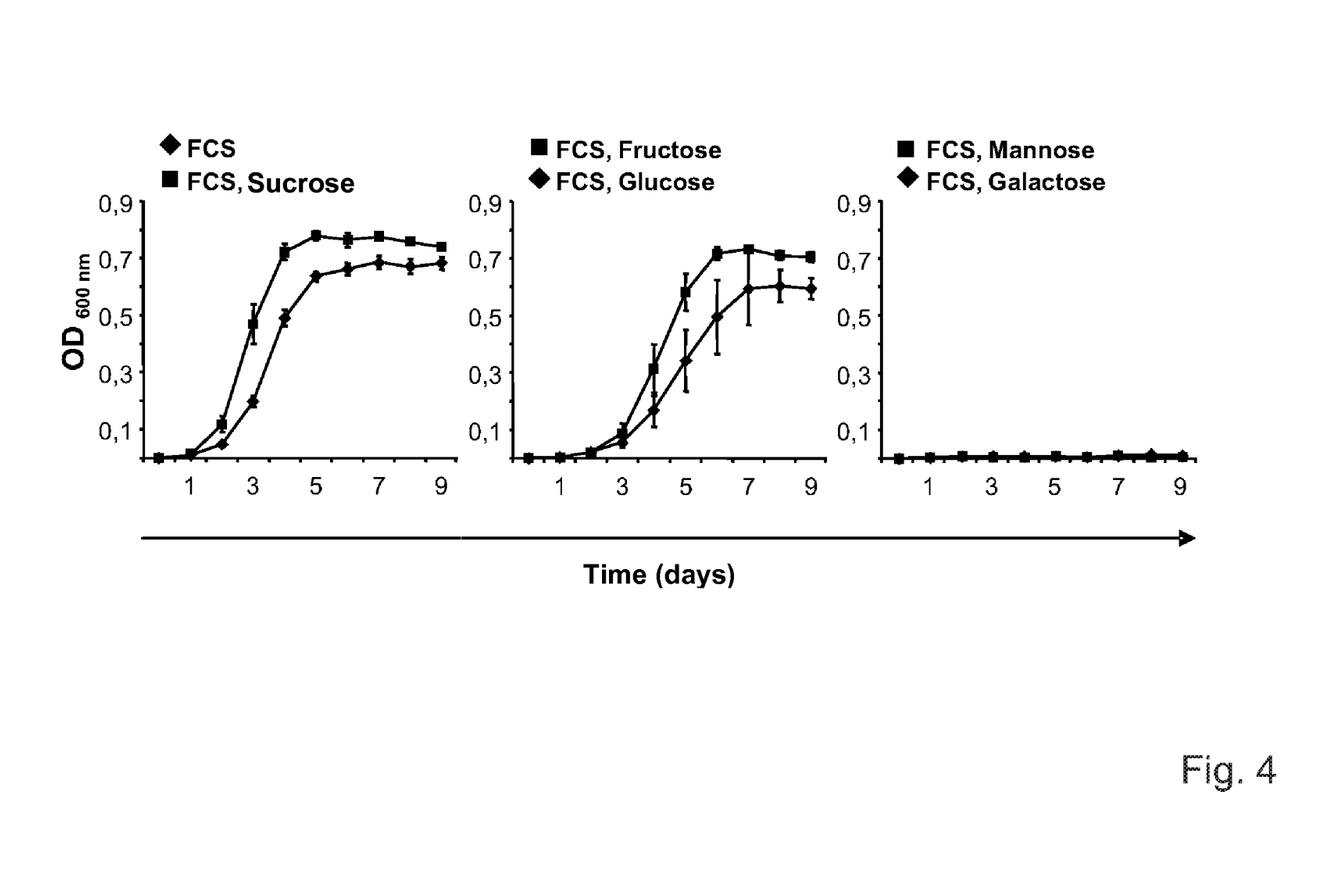
FIG. 4: Improvement of Schneider's medium by supplementation with different sugars. Schneider's medium containing 10 vol.-% FCS was supplemented with 5% (w/v) sucrose, fructose, glucose, mannose or galactose, respectively, and inoculated with *Bartonella henselae* ($1 \times 10^6$/ml). The bacterial growth was determined by measuring the optical density (OD$_{600\ nm}$) at 24 h intervals. It is to be noted that the highest growth rates and the maximum optical densities were obtained with Schneider's medium containing 10 vol.-% FCS and 5% (w/v) sucrose.

For this purpose, Schneider's medium containing 10 vol.-% FCS was supplemented with 5% (w/v) sucrose, fructose, glucose, mannose, or galactose, respectively. The media were inoculated with *Bartonella henselae* ($1\times10^6$/ml) and the bacterial growth was determined by measuring the optical density (FIG. 4).

The data revealed that the addition of sucrose increased growth rates of *Bartonella henselae*, whereas fructose showed no significant effect. Remarkably, the addition of mannose or galactose suppressed the growth of *Bartonella henselae* completely, possibly because of toxic effects.

Figure 5:
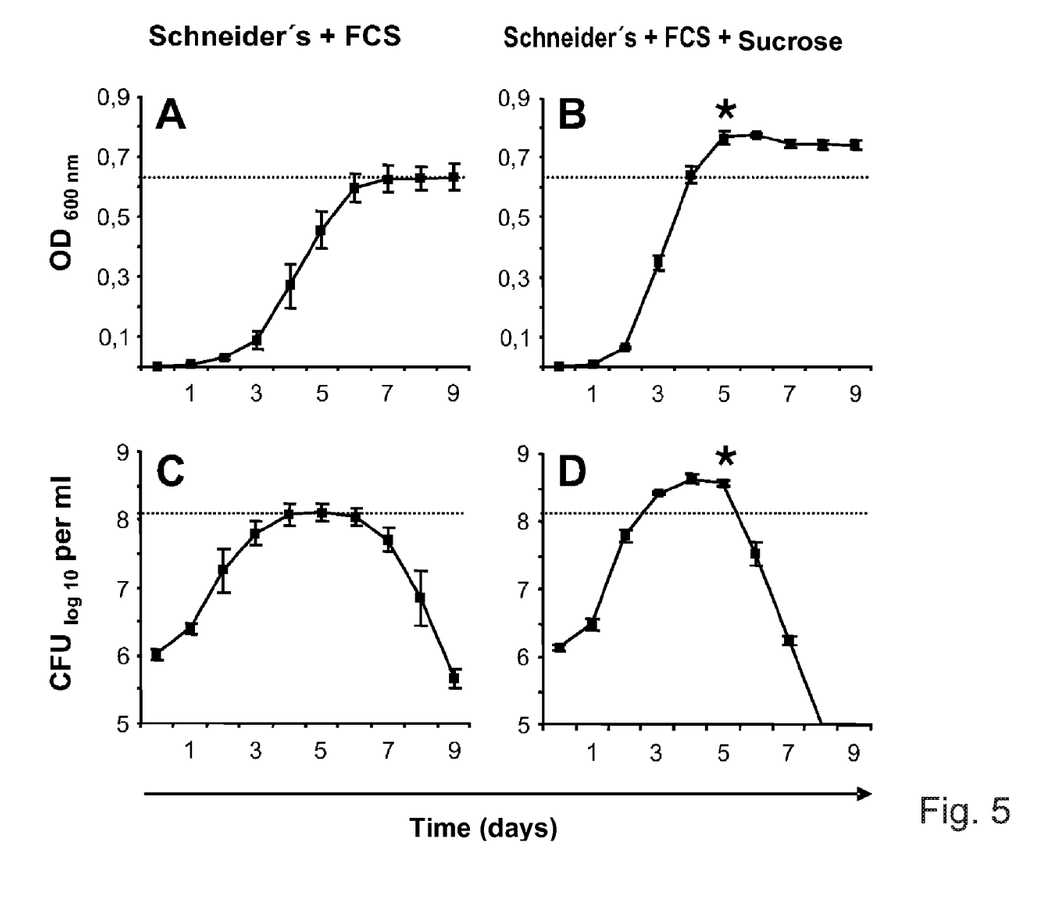
FIG. 5: Comparison of the growth rates in Schneider's medium containing 10 vol.-% FCS depending on the addition of sucrose. The media were inoculated with *Bartonella henselae* ($1\times10^6$/ml) and the bacterial growth was determined by either measuring the optical density ($OD_{600\,nm}$; A, B) or by quantifying the number of viable bacteria (CFU/ml) at 24 h intervals (C, D). It is to be noted that the bacterial growth rates and the maximum number of viable bacteria are higher in the presence of sucrose. * significant difference of maximum OD (p=0.001) or CFU (p=0.004) compared with medium lacking sucrose (day 5).

As significant differences between the optical densities and the numbers of viable bacteria was observed (see FIG. 2), both values were also determined in Schneider's medium containing 10 vol.-% FCS either with or without 5% (w/v) sucrose (FIG. 5). In accordance with the optical density, the maximum bacterial number was ~3.3-fold higher when sucrose was added. Again, a rapid decrease was observed in the number of viable bacteria (death phase) after the exponential growth phase. From these data, the maximum growth rate between day one and two allows to calculate a generation time of approximately 5.6 hours [calculation of generation time: $1\times lg2(t-t_0)/lgN-lgN_0$] in Schneider's medium containing 10 vol.-% FCS and 5% (w/v) sucrose.

Figure 6:
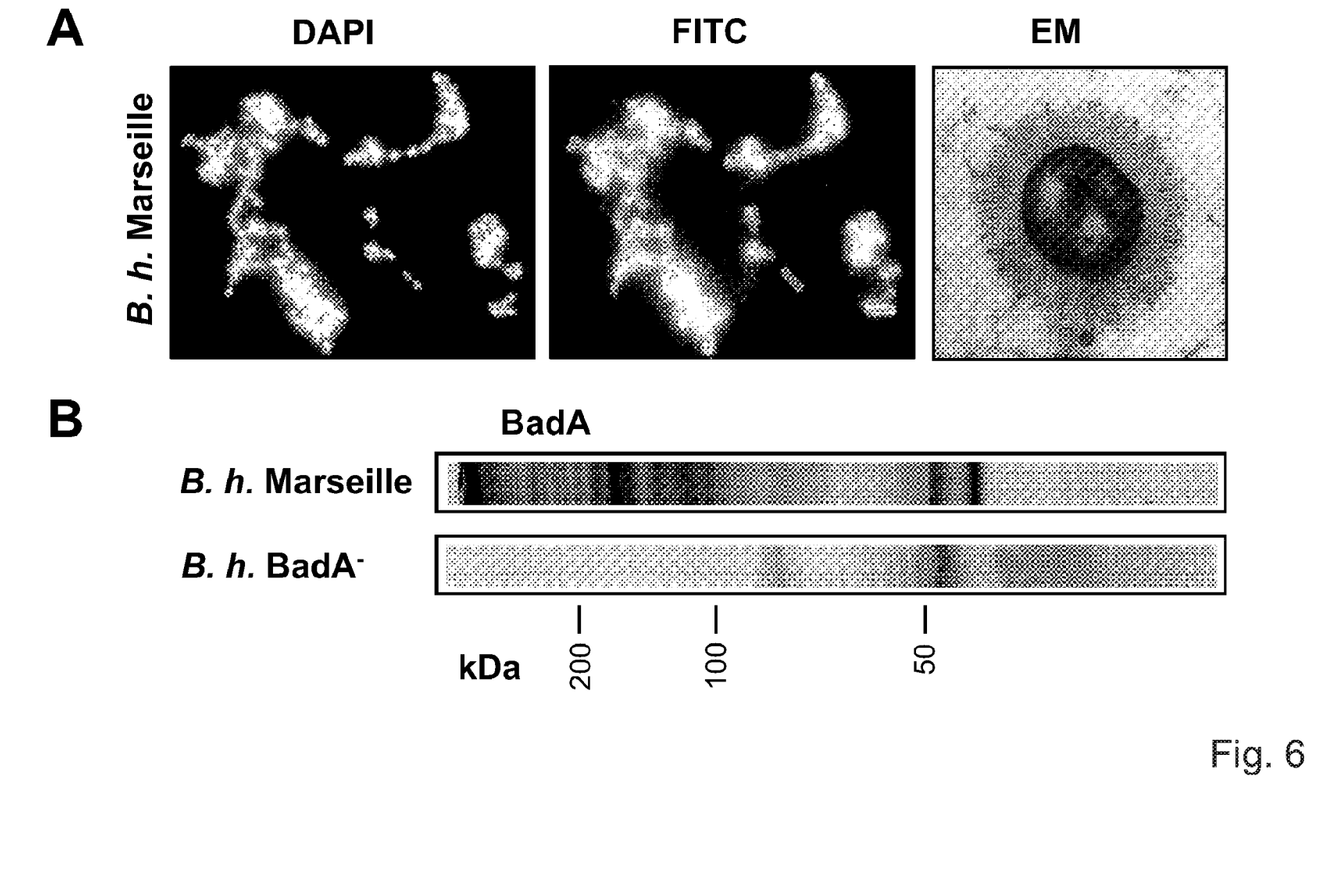
FIG. 6: BadA expression of *Bartonella henselae* grown in Schneider's based *Bartonella* growth medium. (A) *Bartonella henselae* Marseille was grown in Schneider's medium containing 10 vol.-% FCS and 5% (w/v) sucrose and the BadA expression was analyzed by BadA immunostaining and electron microscopy (long "hairy" structures). (B) Detection of BadA in liquid culture supernatants of *Bartonella henselae* Marseille by BadA immunoblotting. *Bartonella henselae* BadA⁻ was used as negative control.

2.4 BadA Expression of *Bartonella henselae* Grown in Schneider's Based *Bartonella* Growth Medium As it is known that the expression of *Bartonella* adhesin A (BadA), an important pathogenicity factor of *Bartonella henselae*, depends on cultivation procedures, the growth of *Bartonella henselae* Marseille in the liquid medium according to the invention was analyzed for the expression of BadA. The immunofluorescence using specific BadA antibodies and electron microscopy (FIG. 6A) demonstrated a strong surface expression. BadA was also detected in the supernatants of the *Bartonella henselae* cultures grown in Schneider's medium containing 10 vol.-% FCS by immunoblotting with specific anti-BadA-antibodies (FIG. 6B). Here, the typical ladder-like pattern of BadA-bands was detectable known to be absent in *Bartonella henselae* BadA$^-$. Similar results were obtained when sucrose was added to the medium (data not shown).

2.5 Functional Analysis of *Bartonella henselae* Grown in Schneider's Based *Bartonella* Growth Medium

Figure 7:
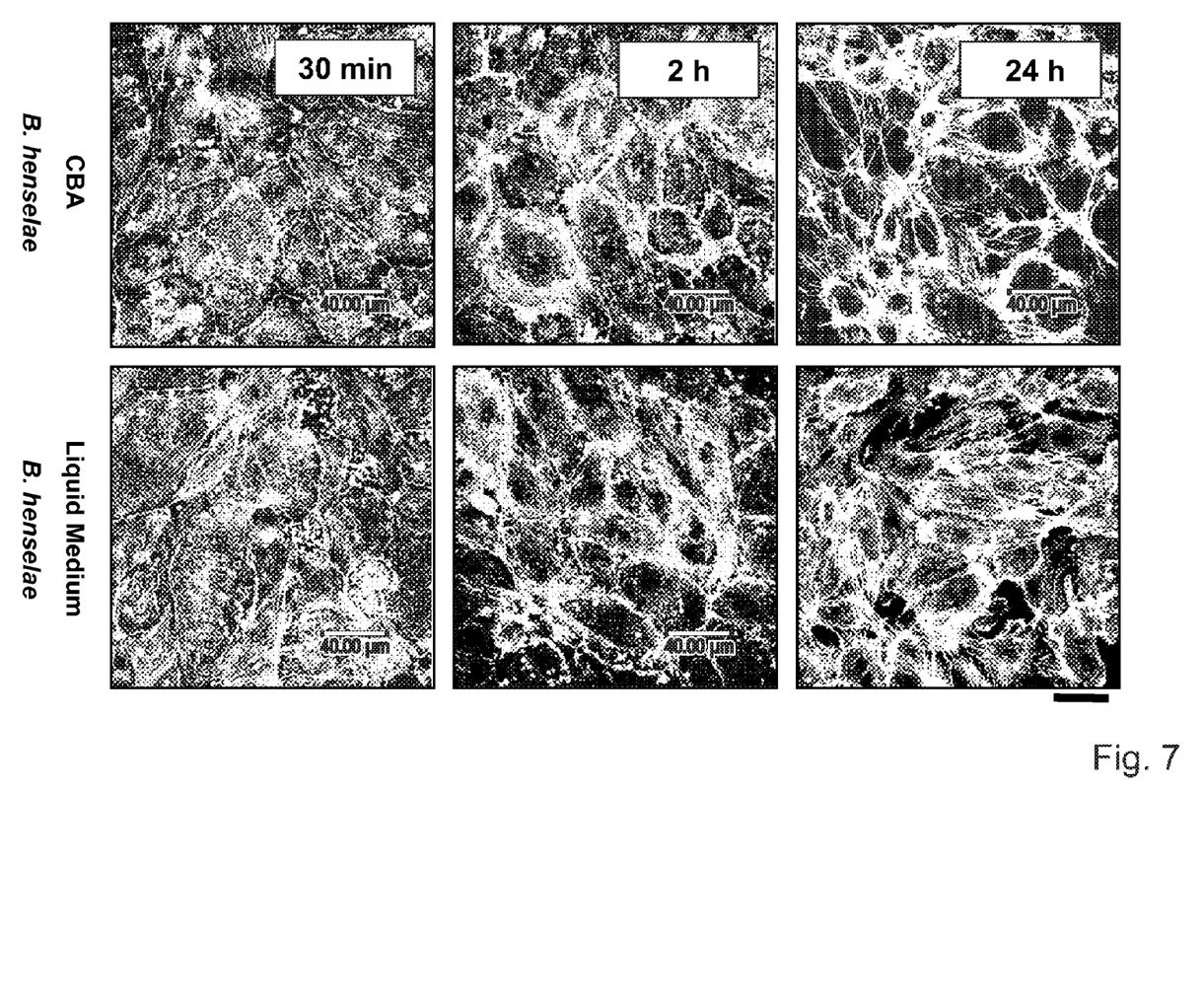
FIG. 7: Host cell adhesion and invasion of *Bartonella henselae* grown in Schneider's based *Bartonella* growth medium. HUVECs were infected with *Bartonella henselae* either grown on CBA or in Schneider's medium containing 10 vol.-% FCS and 5% (w/v) sucrose. Extra- and intracellular bacteria were visualized by CLSM 30 minutes, 2 hours and 24 hours after the infection. Filamentous actin was stained with TRITC-labeled phalloidin. Scale bar: 40 µm.

*Bartonella henselae* adheres to and invades into endothelial cells and induces the secretion of vascular endothelial growth factor VEGF-A; (Kempf, V. A. et al. (2001), Evidence of a leading role for VEGF in *Bartonella henselae*-induced endothelial cell proliferations. Cell. Microbiol. 3:623-632). Therefore, the host cell interaction of *Bartonella henselae* grown on CBA or in liquid medium was analyzed. First, HUVECs were infected with *Bartonella henselae* either grown on CBA or in Schneider's medium containing 10 vol.-% FCS and 5% (w/v) sucrose. The adhesion and invasion was analyzed 30 minutes, 2 hours and 24 hours after the infection by CLSM (FIG. 7). No difference could be observed in the amount of adherence and intracellular *Bartonella henselae*, independent of the particular growth conditions.

Figure 8:
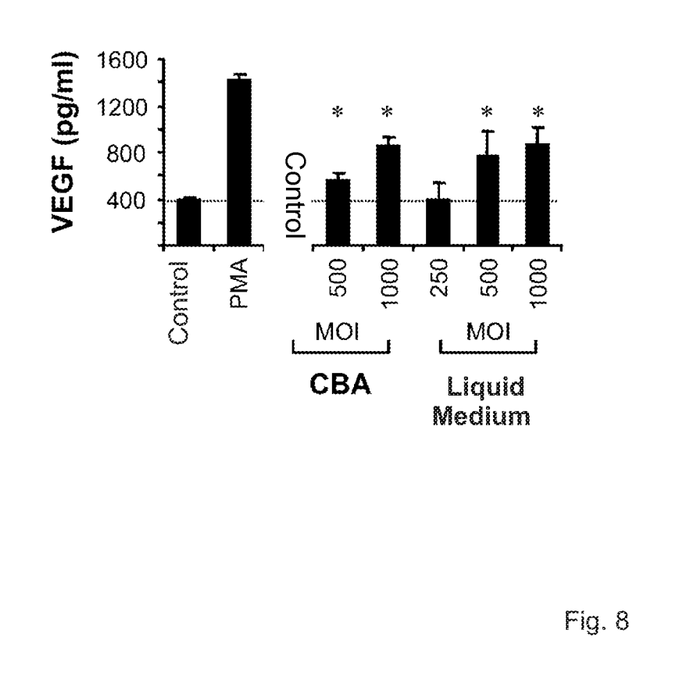
FIG. 8: Induction of the VEGF-A secretion by *Bartonella henselae* grown in Schneider's medium. HeLa 299 cells were infected with *Bartonella henselae* either grown on CBA or in Schneider's medium containing 10 vol.-% FCS and 5% (w/v) sucrose (MOI: 200, 500 and 1000). PMA (25 ng/ml) was used as positive control. VEGF-A was quantified from cell culture supernatants 24 h after the infection by ELISA. It is to be noted that no significant differences in the ability to trigger the VEGF secretion were observed between bacteria grown on agar or on liquid culture. Control: uninfected cells. * significant difference compared with control (p<0.05).

Next, the ability of *Bartonella henselae* to induce the secretion of VEGF-A by infected host cells was analyzed. HeLa cells were infected with *Bartonella henselae* and the VEGF-A concentrations in the supernatants were compared 24 hours after the infection (FIG. 8). The data revealed that similar amounts of VEGF-A were secreted in both experimental settings independent from the growth conditions of the bacteria.

3. Conclusion

The inventors provide for the first time a composition for the cultivation of sophisticated bacteria which enables a rapid growth.

The invention claimed is:

1. Method for the cultivation of sophisticated bacteria, comprising the following steps,
   (1) providing a composition for the cultivation of sophisticated bacteria,
   (2) inoculating the composition with sophisticated bacteria,
   (3) incubating the composition with the bacteria under cultivation conditions,
   wherein the composition comprises modified Schneider's Drosophilia medium and fetal calf serum (FCS), and wherein the sophisticated bacteria are of the genus selected from the group consisting of: *Bartonella, Bordetella* spp., *Borrelia* spp., *Anaplasma* spp. and *Mycobacterium* spp.

2. The method of claim 1, wherein the sophisticated bacteria are such of the genus *Bartonella*.

3. The method of claim 1, wherein the composition contains the following components:

| Inorganic salts, namely | |
| --- | --- |
| $CaCl_2$ (anhydrous) [in mg/l $H_2O$]: | approx. 50 to approx. 2000, |
| KCl [in mg/l $H_2O$]: | approx. 200 to approx. 3000, |
| $KH_2PO_4$ [in mg/l $H_2O$]: | approx. 30 to approx. 1500, |
| $MgSO_4 \cdot 7H_2O$ [in mg/l $H_2O$]: | approx. 1000 to approx. 6000, |
| NaCl [in mg/l $H_2O$]: | approx. 300 to approx. 4000, |
| $NaHCO_3$ [in mg/l $H_2O$]: | approx. 25 to approx. 1300, |
| $Na_2HPO_4$ [in mg/l $H_2O$]: | approx. 60 to approx. 2500, |
| amino acids, namely | |
| β-alanine [in mg/l $H_2O$]: | approx. 30 to approx. 1800, |
| L-arginine [in mg/l $H_2O$]: | approx. 50 to approx. 2000, |
| L-aspartic acid [in mg/l $H_2O$]: | approx. 25 to approx. 1300, |
| L-cysteine [in mg/l $H_2O$]: | approx. 5 to approx. 200, |
| L-cysteine•2HCl [in mg/l $H_2O$]: | approx. 2 to approx. 150, |
| L-glutamine [in mg/l $H_2O$]: | approx. 250 to approx. 3500, |
| L-glutamic acid [in mg/l $H_2O$]: | approx. 75 to approx. 2600, |
| glycine [in mg/l $H_2O$]: | approx. 20 to approx. 1000, |
| L-histidine [in mg/l $H_2O$]: | approx. 25 to approx. 1300, |
| L-isoleucine [in mg/l $H_2O$]: | approx. 10 to approx. 400, |
| L-leucine [in mg/l $H_2O$]: | approx. 10 to approx. 400, |
| L-lysine•HCl [in mg/l $H_2O$]: | approx. 200 to approx. 3000, |
| L-methionine [in mg/l $H_2O$]: | approx. 10 to approx. 400, |
| L-proline [in mg/l $H_2O$]: | approx. 250 to approx. 3500, |

-continued

| | |
| --- | --- |
| L-serine [in mg/l $H_2O$]: | approx. 20 to approx. 1000, |
| L-threonine [in mg/l $H_2O$]: | approx. 25 to approx. 1300, |
| L-tryptophan [in mg/l $H_2O$]: | approx. 10 to approx. 400, |
| L-tyrosine [in mg/l $H_2O$]: | approx. 30 to approx. 1800, |
| L-valine [in mg/l $H_2O$]: | approx. 20 to approx. 1000, |
| other components, namely | |
| malic acid [in mg/l $H_2O$]: | approx. 5 to approx. 200, |
| succinic acid [in mg/l $H_2O$]: | approx. 50 to approx. 2000, |
| fumaric acid [in mg/l $H_2O$]: | approx. 5 to approx. 200, |
| glucose [in mg/l $H_2O$]: | approx. 300 to approx. 4000, |
| yeast extract [in mg/l $H_2O$]: | approx. 300 to approx. 4000, |
| α-ketoglutaric acid [in mg/l $H_2O$]: | approx. 25 to approx. 1300, |
| α-trehalose [in mg/l $H_2O$]: | approx. 300 to approx. 4000, and |
| fetal calf serum (FCS) [in vol.-%] | approx. 1 to approx. 25. |

4. The method of claim 1, wherein the composition contains the following components:

| Inorganic salts, namely | |
| --- | --- |
| $CaCl_2$ (anhydrous) [in mg/l $H_2O$]: | approx. 600, |
| KCl [in mg/l $H_2O$]: | approx. 1600, |
| $KH_2PO_4$ [in mg/l $H_2O$]: | approx. 450, |
| $MgSO_4 \cdot 7H_2O$ [in mg/l $H_2O$]: | approx. 3700, |
| NaCl [in mg/l $H_2O$]: | approx. 2100, |
| $NaHCO_3$ [in mg/l $H_2O$]: | approx. 400, |
| $Na_2HPO_4$ [in mg/l $H_2O$]: | approx. 700, |
| amino acids, namely | |
| β-alanine [in mg/l $H_2O$]: | approx. 500, |
| L-arginine [in mg/l $H_2O$]: | approx. 600, |
| L-aspartic acid [in mg/l $H_2O$]: | approx. 400, |
| L-cysteine [in mg/l $H_2O$]: | approx. 60, |
| L-cysteine•2HCl [in mg/l $H_2O$]: | approx. 21.7, |
| L-glutamine [in mg/l $H_2O$]: | approx. 1800, |
| L-glutamic acid [in mg/l $H_2O$]: | approx. 800, |
| glycine [in mg/l $H_2O$]: | approx. 250, |
| L-histidine [in mg/l $H_2O$]: | approx. 400, |
| L-isoleucine [in mg/l $H_2O$]: | approx. 150, |
| L-leucine [in mg/l $H_2O$]: | approx. 150, |
| L-lysine•HCl [in mg/l $H_2O$]: | approx. 1650, |
| L-methionine [in mg/l $H_2O$]: | approx. 150, |
| L-proline [in mg/l $H_2O$]: | approx. 1750, |
| L-serine [in mg/l $H_2O$]: | approx. 250, |
| L-threonine [in mg/l $H_2O$]: | approx. 350, |
| L-tryptophan [in mg/l $H_2O$]: | approx. 100, |
| L-tyrosine [in mg/l $H_2O$]: | approx. 500, |
| L-valine [in mg/l $H_2O$]: | approx. 300, |
| other components, namely | |
| malic acid [in mg/l $H_2O$]: | approx. 60, |
| succinic acid [in mg/l $H_2O$]: | approx. 600, |
| fumaric acid [in mg/l $H_2O$]: | approx. 60, |
| glucose [in mg/l $H_2O$]: | approx. 2000, |
| yeast extract [in mg/l $H_2O$]: | approx. 2000, |
| α-ketoglutaric acid [in mg/l $H_2O$]: | approx. 350, |
| α-trehalose [in mg/l $H_2O$]: | approx. 2000, and |
| fetal calf serum (FCS) [in vol.-%] | approx. 10. |

5. The method of claim 1, wherein the composition additionally comprises approximately 0.5 to approximately 50% (w/v) sucrose.

6. The method of claim 1, wherein the composition comprises approximately 5% (w/v) sucrose.

7. The method of claim 1, wherein the composition comprises a pH value of approximately 5.5 to approximately 7.5.

8. The method of claim 1, wherein the composition comprises a pH value of approximately 6.5.

9. The method of claim 1, wherein the composition is sterilized.

\* \* \* \* \*